United States Patent
Coats

(10) Patent No.: US 9,797,689 B2
(45) Date of Patent: Oct. 24, 2017

(54) PERSONAL ARMOR WITH PERFORMANCE DESTRUCTION TEST COUPONS

(71) Applicant: PHALANX DEFENSE SYSTEMS, LLC, Gainesville, FL (US)

(72) Inventor: James Coats, Gainesville, FL (US)

(73) Assignee: PHALANX DEFENSE SYSTEMS LLC, Gainesville, FL (US)

( * ) Notice: Subject to any disclaimer, the term of this patent is extended or adjusted under 35 U.S.C. 154(b) by 204 days.

(21) Appl. No.: 14/770,129

(22) PCT Filed: May 22, 2015

(86) PCT No.: PCT/US2015/032208
§ 371 (c)(1),
(2) Date: Aug. 25, 2015

(87) PCT Pub. No.: WO2016/018497
PCT Pub. Date: Feb. 4, 2016

(65) Prior Publication Data
US 2016/0273882 A1    Sep. 22, 2016

Related U.S. Application Data

(60) Provisional application No. 62/031,228, filed on Jul. 31, 2014.

(51) Int. Cl.
| F41H 1/02 | (2006.01) |
| G01N 3/30 | (2006.01) |
| G01N 3/313 | (2006.01) |

(52) U.S. Cl.
CPC ............ *F41H 1/02* (2013.01); *G01N 3/30* (2013.01); *G01N 3/313* (2013.01)

(58) Field of Classification Search
CPC ............ F41H 1/02; G01N 3/30; G01N 3/313
See application file for complete search history.

(56) References Cited

U.S. PATENT DOCUMENTS

| 4,079,464 A * | 3/1978 | Roggin | .................... F41H 1/02 |
| | | | 2/2.5 |
| 4,530,111 A * | 7/1985 | Barron | .................... F41H 1/02 |
| | | | 2/2.5 |
| 2009/0320171 A1 * | 12/2009 | Kocher | .................... F41H 1/02 |
| | | | 2/2.5 |

(Continued)

OTHER PUBLICATIONS

Withnall, Christopher; "Aged Armour Testing Study;" May 2010; Biokinetics and Associated Ltd.*

(Continued)

*Primary Examiner* — Daniel J Colilla
(74) *Attorney, Agent, or Firm* — Sven W. Hanson

(57) ABSTRACT

A personal ballistic protection device incorporates multiple removable test coupons. Each of the test coupons are retained with the ballistic device during its use until each coupon is removed for test purposes. Each test coupon has a construction identical to the protective portions of the ballistic device and is removable and configured to allow for destructive testing. Sufficient coupons are provided with the ballistic protection device to allow for periodic testing over a predetermined useful life of the ballistic protection device. One embodiment of the device is a body armor vest.

1 Claim, 3 Drawing Sheets

(56) References Cited

U.S. PATENT DOCUMENTS

| | | | |
|---|---|---|---|
| 2011/0023201 A1* | 2/2011 | Pearl | F41H 1/02 |
| | | | 2/2.5 |
| 2012/0159680 A1* | 6/2012 | Howland | F41H 1/02 |
| | | | 2/2.5 |
| 2016/0146579 A1* | 5/2016 | Alaniz | F41H 5/02 |
| | | | 89/36.02 |

OTHER PUBLICATIONS

Body Armor Model Policy; Missouri Police Chiefs Association; found at http://www.mopca.com/mpca.nsf/str/BCO2F4E07567FC50862577E3006CCABC/%file/Vol%201%20Body%20armor.doc; Dec. 1989.*

* cited by examiner

PERSONAL ARMOR WITH PERFORMANCE DESTRUCTION TEST COUPONS

BACKGROUND

The present invention pertains to personal body armor, particularly, garments such as vests that incorporate protective structures that prevent or reduce injury from striking ballistic projectiles such as firearms weapons and the like. Herein, the term "ballistic" means elements or constructions providing substantial such properties.

In the past, many ballistic protection devices have been constructed with high-strength materials such as aramid fibers, plastics, and other materials of relatively complex chemical makeup. One drawback of using these materials is their relative instability over their use life due to exposure to changing and various ambient conditions such as high humidity, high moisture, temperature fluctuation and solar exposure. Changes in material properties as a result of these conditions have the potential of reducing effectiveness.

In other applications of these materials, periodic testing may be used to verify that the material properties are maintained within defined requirements or limits. In applications for ballistic protection devices, the most relevant test is performance in actual resistance to ballistic impact. However, the destructive nature of such testing inevitably renders the tested article unable for continued use. What is desired is a ballistic protection device construction and system that allows destructive performance testing of the ballistic protection elements while protecting and retaining the performance capability of the ballistic protection device.

SUMMARY OF THE INVENTION

The invention is a device and system that incorporates multiple test coupons in the construction of a personal ballistic protection device. Each of the test coupons is retained with the protection device during the useful life of the protective device until the coupons are individually removed for test purposes. Each test coupon has a construction identical to the protective portions of the protective device and is easily removable and configured to allow for destructive testing. Sufficient multiple coupons are provided with each ballistic protection device over its life to allow for periodic testing over a predetermined useful life of the ballistic protection device.

The ballistic protection device may be embodied as a garment such as a vest, however, the same construction and methods may be used with other ballistic protection devices. In a preferred embodiment, a vest garment is configured to be worn by a user. The vest includes front and back portions that may be separable for convenience. Each portion includes a flexible cover that may include fasteners and other convenience elements. The cover is configured to accept a respective removable shield having ballistic properties. Each shield includes attached test coupons formed of a construction identical to the shield. Each test coupon is removable and the respective shield cover configured for removal of each test coupon. Other configurations, including those incorporating future developed materials and shield constructions, yet using the inventive aspects herein define, and contemplated and within the scope of the invention. Further aspects of the invention are clarified in the following discussion of embodiments and in the associated drawing figures.

DETAILS OF EMBODIMENTS OF THE INVENTION

Figure 1:
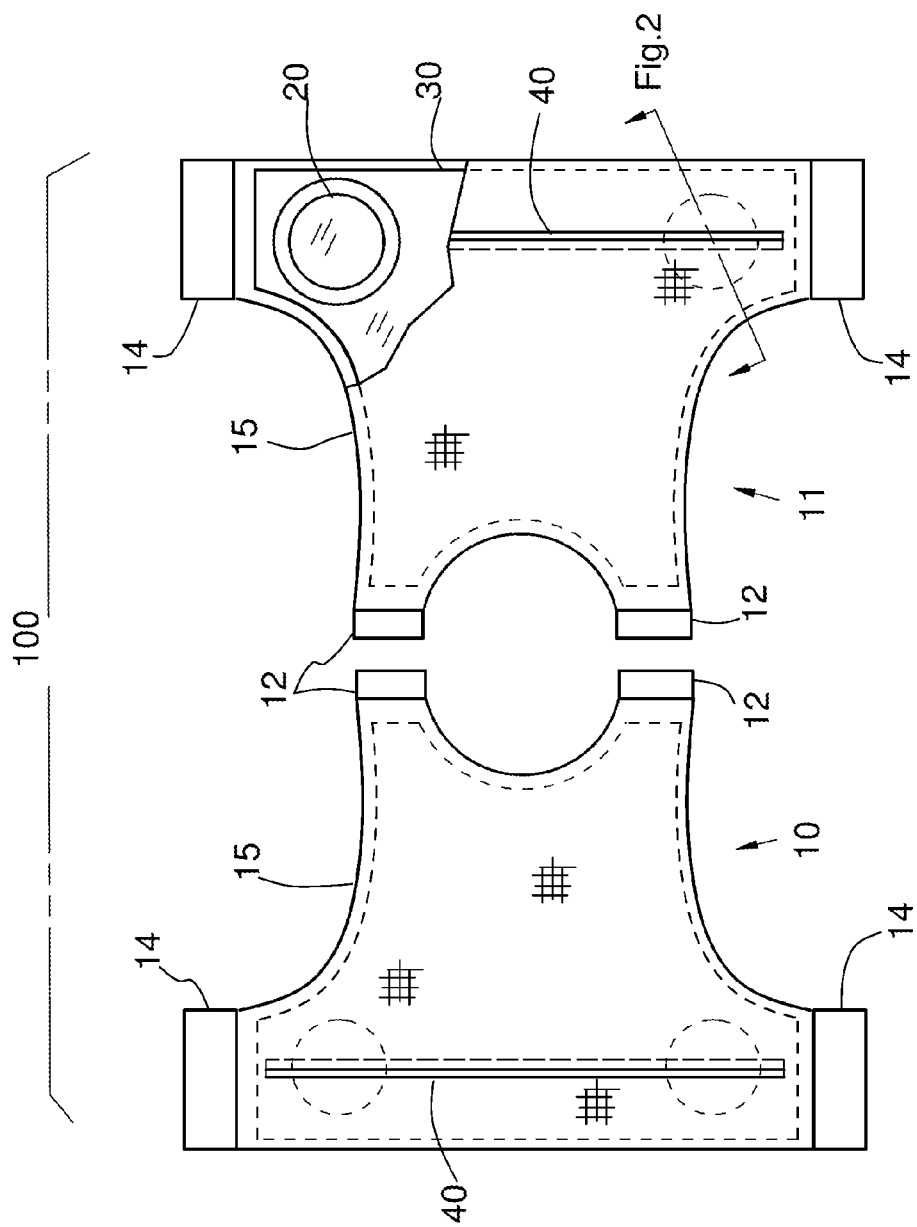
FIG. 1 is plan view of one embodiment of a personal protection vest according to the invention.
Figure 2:
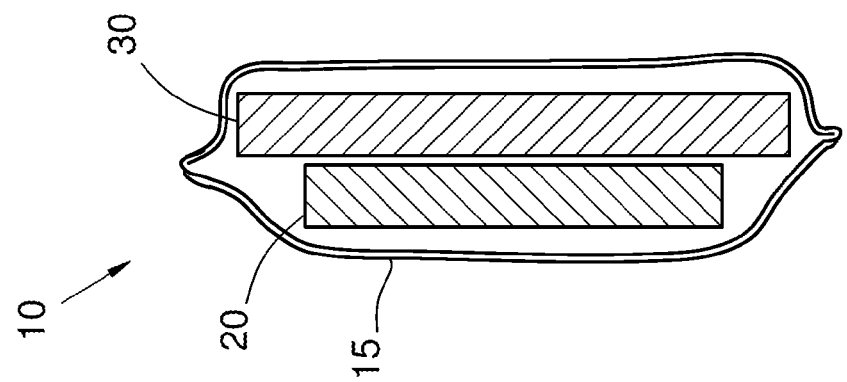
FIG. 2 is a detailed section view on one portion of the construction of FIG. 1.

FIG. 1 is a plan view of a preferred embodiment of the invention in the form of a body armor vest 100 configured to be worn on the upper torso in the manner of a conventional vest garment. The vest includes two separable garment portions 10, 11. They are separable for improved ease of manufacture, assembly and use. FIG. 2 is a section view of one portion (details of the elements in FIG. 2 are discussed below in regard to FIG. 4). The two portions 10, 11 are configured to be joined to form, respectively, the anterior and posterior elements of the vest when worn by a human user.

Each of the two portions 10, 11 are preferably functionally identical and differ only in the nature of their respective mating connecting elements. However, they need not be identical in shape and size and may be altered in these aspects for convenience or alternation of positioning on the user.

Each of the portions 10, 11 includes an outer covering 15 that serves as the main garment element and provides general covering of the user, support for the ballistically functional elements and interconnectivity. For these purposes the covering 15 may be any of a variety of conventional durable flexible fabrics used in the prior art for garmets or safety vests or protection garments, or materials with similar properties.

The portions 10, 11 and respective coverings 15 should include respective shoulder sections configured to cojoin using first fastening elements 12. These fastening elements 12 may be formed of industrial grade "hook and loop" elements, or other devices providing similar function. The portions 10, 11 and respective coverings 15 also include waist sections configured to cojoin using second fastening elements 14 having similar properties and function as the first fastening elements 12. In this way the two portions 10, 11 maybe each assembled as a generally planar element and then the two cojoined on the user to form a body-enclosing barrier for the upper torso.

Figure 3:
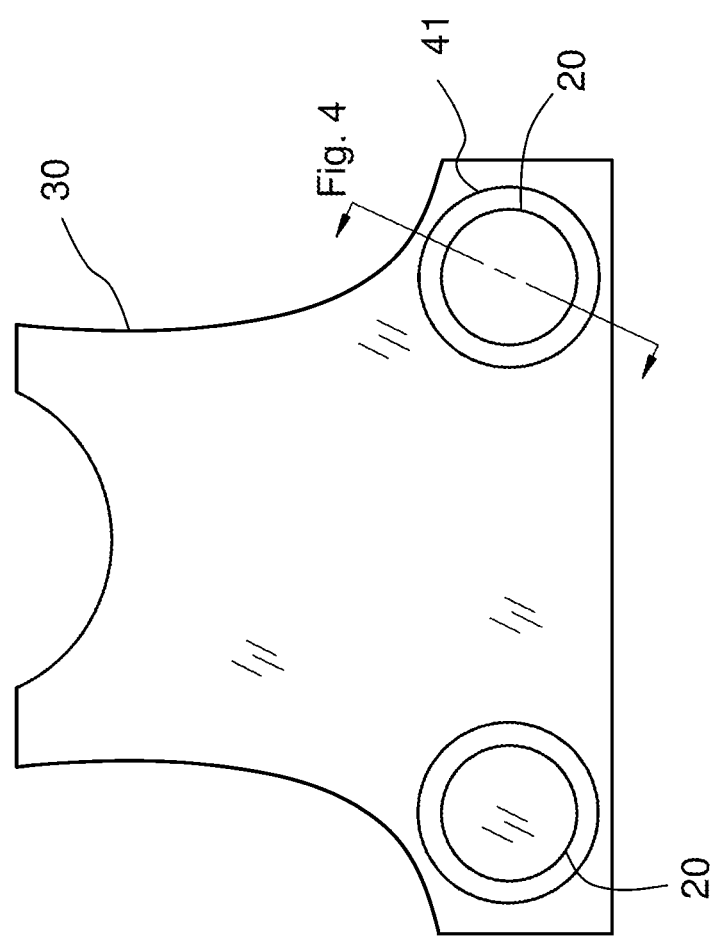
FIG. 3 is a plan view of a ballistic insert incorporated in the construction of the embodiment of FIG. 1.

Each portion 10, 11 includes a ballistic shield 30 that is enclosed within the respective covering 15. The shield 30 is shown in more detail in FIG. 3; this construction is common for the shields in each of the portions 10, 11 in the embodiment illustrated. However, distinct shaped shields may be used where the portions 10, 11 have different shapes. The particular preferred construction of the ballistic shield 30 is detailed below, but generally is configured to provide a specific level of resistance against incident ballistic projectiles for the user while the vest is worn as intended. The overall shape of the shield 30 generally should be maximally extentive over the area of the portions 10, 11 to provide a maximum of ballistic protection to the user. The critical user body areas for protection are known and defined in the prior art. Preferably, in all cases, each portion 10, 11 and shield 30 is shaped and configured to overall a substantial body portion of the intended user's body.

As a convenience, the cover 15 of each portion 10, 11 may include a sealable overlapping opening slit 40 sized and configured to allow passage of the respective shield 30 into and out of the portion 10, 11 both for initial assembly and for removal of test coupons (described below). The slit 40 may have any of a variety of configurations and may be sealed by any of a number of convention devices or methods.

A section of the covering 15 is cut away in FIG. 1 to illustrate the shield 30 and one of four test coupons 20. Each shield 30 includes two coupons in the general manner shown in FIG. 3. Preferably each test coupon 20 is located generally in waist sections for a variety of purposes, including comfort.

Figure 4:
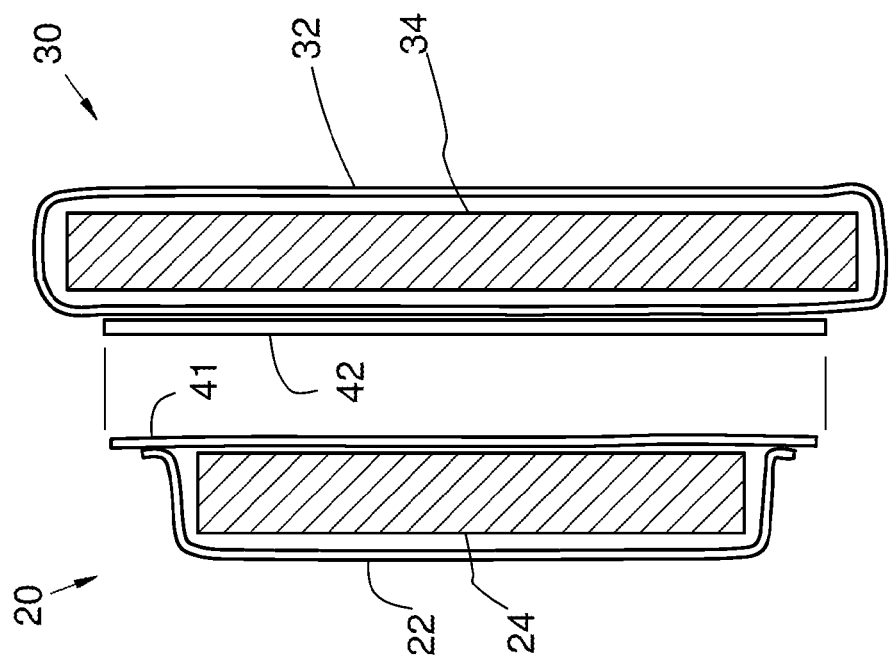
FIG. 4 is a detailed section view of one portion of the device of FIG. 3.

FIG. 4 is a section view of a shield 30 including a test coupon 20. In FIG. 4, the test coupon 20 is separated from the shield 30 for illustration purposes, but it should be clear that each test coupon 20 is physically connected to it's respective shield 30.

Referring particularly to FIG. 4, each shield 30 includes a shield body 34 that provides the ballistic properties required and a flexible wrap 32. The wrap 32 is formed of a flexible material selected to provide an environmental barrier and protection to the shield body 34. For those purposes the wrap may have any of varias different properties depending on the constituent materials of the shield body 34. The wrap also provides a convenient handling covering for the shield. Alternatively, the wrap 32 may be an integral element of the shield body 34.

Each test coupon 20 includes a coupon body 24 having a construction identical to that of the shield body 34. Preferably, the coupon body 24 is cut from the same material stock as the shield body 34. Each test coupon 20 preferably includes a coupon covering 22 as a protective element and convenience for handling the coupon body 24. For each test coupon 20, a securing device is provided for securing the test coupon against the shield 30 in the desire location. In the embodiment shown, the securing device is provided by mating "hook and loop" fabric portions 41, 42 attached or integrated into, the test coupon 20 and shield 30. The securing device may take other forms of devices and methods with a common critical function of allowing easy removal of the test coupon 20 after use.

Preferably at least four test coupons 20 are provided with each set of portions 10, 11 forming a vest. The purpose for this configuration is to enable useful destructive testing of coupons over the useful life of the vest. It is known that a four to five year use life is conventional in police and military applications.

In use, approximately one year after a vest as specified here is put into intended use, one test coupon 20 is removed from the vest. The test coupon 20 may then be subjected to any selected testing processes, including destructive testing. Preferably, the test coupon is subjected to a function test of firing a ballistic weapon at the test coupon 20 in a manner functionally simulating the intended use of the vest for user personal protection. This process may be repeated every year for an additional three years. If the selected test critierion is met, the vest may then be continued in use for an additional time, providing a tested useful life of greater than four years. Because removal of the test coupon 20 does not regrade the shield 30 itself, testing may be carried out without reducing the useful like of the article. It should be clear that the function of the test coupon 20 is the same for configurations including one or more than four coupons.

An additional benefit of the introduction of the test coupons to the ballistic shield 30 is the resulting standoff spacing of the covering 15 from the shield 30 inside of each portion 10, 11. That is, the increase thickness of the test coupon over the shield 30 separates the covering 15 from the shield 30 in the areas surrounding the test coupon 20. This results in a gap between the covering 15 and the shield 30 over a substantial area of the portions 10, 11. If the covering 15 is formed of fabric that allows each airflow through the covering 15, air may circulate through this gap to enhance evaporation and cooling. For this reason, the test coupons 20 are preferably located on the outside surface of the shield 30, although they may also be located on the inside (closer to the user's body).

Preferably, the shield body 34, and hence test coupon body 24 are formed of a multilayer construction of substantially high-strength sheet materials. In many convention ballistic shield devices, materials formed of aramid fabrics or other forms of aramid materials. Aramids are generally materials generally prepared by the reaction between an amine group and a carboxylic acid halide group. These materials includes meta-aramids such as that sold under the trademark Kevlar by the United States company, E. I. du Pont de Nemours and Company. In the following, the term "aramid" refers to an element formed substantially by at least one form aramid material, or other material having like properties. The preferred construction of the shield body 34 (and hence the test coupon body 24) is a twenty-one layer assembly including: two outer (strike face) layers, each strike face layer including two sheets of woven aramid laminated together with a film layer between them (total weight/area density of 0.135 pounds per square foot). The film layer is substantially polyethylene. Behind the strike face are eighteen layers of unidirectional aramid material. This material is preferably a material supplied under the trademark Gold Flex by the Honeywell International Inc. company. Behind these is at least one layer of the same material as specified for the strike face. They are preferably not stitched together or otherwise interconnected. The assembled construction is secured within the shield cover 32 (or coupon cover 22). While the particular ballistic construction has been shown to be effective, other constructions are possible and may be incorporated in the invention without deviating from the invention.

The above embodiments are provided as illustrative of the features and functions of the invention. One skilled in the art will understand or discover alternative configurations or constructions within the invention as defined by the claims.

The invention claimed is:
1. A method of destruction testing of a ballistic resistant garment, comprising:
   defining a useful life period;
   providing a garment with a ballistic shield having a ballistic construction; removably securing to the garment on multiple test coupons, each test coupon comprising the ballistic construction;
   periodically, during a time equal to the useful life period, removing one test coupon and performing destructive testing on the test coupon.

* * * * *